United States Patent [19]

Cimarusti et al.

[11] 4,018,760

[45] Apr. 19, 1977

[54] THIO-β-LACTAM CEPHALOSPORINS

[75] Inventors: Christopher M. Cimarusti, Hamilton, N.J.; Paul Wojtkowski, Wilmington, Del.; Joseph E. Dolfini, Cincinnati, Ohio

[73] Assignee: E. R. Squibb & Sons, Inc., Princeton, N.J.

[22] Filed: Feb. 20, 1976

[21] Appl. No.: 659,863

Related U.S. Application Data

[62] Division of Ser. No. 551,222, Feb. 19, 1975, Pat. No. 3,971,780.

[52] U.S. Cl. .......................... 260/243 C; 424/246

[51] Int. Cl.[2] .......................... C07D 501/20

[58] Field of Search .......................... 260/243 C

[56] References Cited

UNITED STATES PATENTS 3,971,780 2/1975 Cimarusti .......................... 260/243 C

*Primary Examiner*—Nicholas S. Rizzo
*Attorney, Agent, or Firm*—Lawrence S. Levinson; Merle J. Smith

[57] ABSTRACT

Thio-β-lactam cephalosporins of the general formula

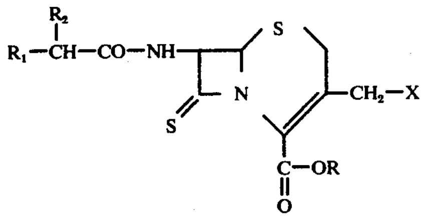

wherein R is hydrogen, lower alkyl, phenyl-lower alkyl, trihaloethyl, alkali metal or alkaline earth metal; $R_1$ is hydrogen, lower alkyl, cycloalkyl, phenyl, phenoxy, phenyl-lower alkyl or certain heterocyclic groups; $R_2$ is hydrogen, amino, carboxy, hydroxy or ureido; and X is hydrogen, hydroxy, lower alkylthio, lower alkylthiadiazolyl, lower alkyltetrazolyl or lower alkanoyloxy, are useful as antimicrobial agents.

9 Claims, No Drawings

THIO-β-LACTAM CEPHALOSPORINS

This is a division of application Ser. No. 551,222, filed Feb. 19, 1975, now U.S. Pat. No. 3,971,780.

SUMMARY OF THE INVENTION

This invention relates to new thio-β-lactam cephalosporins of the formula

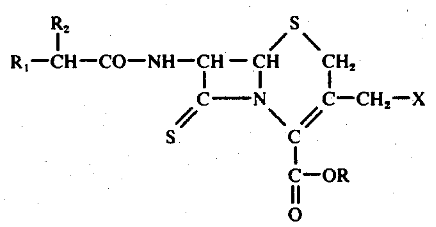
(I)

R represents hydrogen, lower alkyl, phenyl-lower alkyl, trihaloethyl, alkali metal or alkaline earth metal; $R_1$ represents hydrogen, lower alkyl, saturated and unsaturated cycloalkyl, phenyl, phenoxy, phenyl-lower alkyl or certain heterocyclic groups; $R_2$ represents hydrogen, amino, hydroxy, carboxy or ureido; and X represents hydrogen, hydroxy, lower alkylthio, lower alkylthiadiazolyl, lower alkyltetrazolyl or lower alkanoyloxy.

The preferred members within each group are as follows: R is hydrogen, alkali metal or trichloroethyl, especially hydrogen, sodium or potassium; $R_1$ is hydrogen, phenyl, thienyl or furyl, especially phenyl or thienyl; $R_2$ is hydrogen, amino, hydroxy or carboxy, especially hydrogen, hydroxy or amino; and X is hydrogen, acetoxy or 1-methyl-1H-tetrazol-5-ylthio.

DETAILED DESCRIPTION OF THE INVENTION

The various groups represented by the symbols have the meanings defined below and these definitions are retained throughout this specification.

The lower alkyl groups are straight or branched chain hydrocarbon radicals from methyl to heptyl, for example, methyl, ethyl, propyl, isopropyl, butyl, isobutyl, t-butyl, amyl or the like. The one to four carbon groups are preferred, especially methyl and ethyl. The lower alkylthio groups have such alkyl groups linked through a sulfur atom, e.g., methylthio, ethylthio, propylthio, etc., the first being preferred.

The cycloalkyl groups include saturated and unsaturated cyclic groups having three to seven carbon atoms and one or two double bonds, for example, cyclopropyl, cyclobutyl, cyclopentyl, cyclohexyl, cycloheptyl, cyclobutenyl, cyclopentenyl, cyclohexenyl, cyclopentadienyl, cyclohexadienyl and the like. The five and six carbon members are preferred and among the unsaturated members, the 1,4-cyclohexadien-1-yl and 1-cyclohexen-1-yl groups are especially preferred.

The phenyl-lower alkyl groups include a phenyl group attached to a lower alkyl group as described above. Benzyl and phenethyl are preferred.

The lower alkanoyloxy groups are those derived from the lower fatty acids, e.g., acetoxy, propionoxy, butyroxy, etc. The two to four carbon members are preferred, especially acetoxy.

The four common halogens are included in the term "halo," chlorine and bromine, especially chlorine, being preferred.

The heterocyclics represented by $R_1$ are those having 5 or 6 atoms exclusive of hydrogen which are carbon, sulfur, nitrogen and oxygen, no more than two being other than carbon, namely thienyl, furyl, oxazolyl, isoxazolyl and thiazolyl, as well as these heterocyclics with the substituents halo or lower alkyl (particularly methyl and ethyl). The heterocyclic radicals represented by X including lower alkylthiadiazolylthio and lower alkyltetrazolylthio are particularly 5-lower alkyl-1,3,4-thiadiazolyl-2-ylthio and 1-lower alkyl-1H-tetrazol-5-ylthio, especially wherein the lower alkyl group in each instance is methyl.

In addition to hydrogen, R is a salt forming ion, e.g., metal ions, like the alkali metal ions such as sodium or potassium or the alkaline earth metal ions such as calcium or magnesium.

The new cephalosporins of this invention are produced by several alternate routes. A preferred method comprises converting a known cephalosporin, i.e., one having oxygen instead of sulfur in the 8-position corresponding to the formula

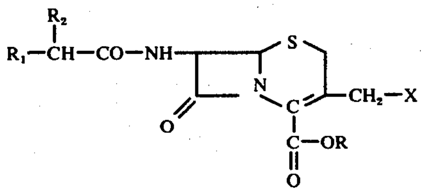
(II)

by reaction with boron sulfide. This reaction is effected by treating the cephalosporin of formula II with an excess of boron sulfide, e.g., about two moles of the boron sulfide to about one mole of cephalosporin compound, in an inert organic solvent such as chloroform, dichloromethane, benzene, or the like. An elevated temperature, e.g., in the range of about 30° to about 80° C. is used. It is desirable, during this reaction, to protect the carboxy group with a protecting group which is then easily removed. Preferred is the formation of the 2,2,2-trichloroethyl ester [which is effected by the method of Chauvette et al., J. Org. Chem. 36, 1259 (1971)]. The protecting group is removed, after the sulfur atom is introduced, by treatment with a metal-acid pair, e.g., an excess of zinc metal in aqueous acetic acid. Other protecting groups which can be used include, for example, dichloroethyl and methyl esters. The product is then isolated and purified by conventional procedures, e.g., filtration, evaporation of solvent, chromatography, etc.

An alternate method comprises first treating a readily available and readily cleavable cephalosporin, such as cephalosporin G, cephalosporin V, or the like, with boron sulfide as described above. Then the product, optionally with the protecting group still in place, is cleaved by known methods, e.g., by conversion to an intermediate imino chloride followed by hydrolysis to remove the acyl group in the 7-position. This provides a new intermediate, which is also part of this invention, having the formula (III)

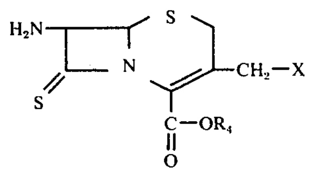

wherein $R_4$ is hydrogen or preferably trichloroethyl. This intermediate can then be acylated with the appropriate acid halide, acid anhydride or acylating combination by conventional techniques to obtain the product of formula I having the desired acyl group in the 7-position.

According to this embodiment the reaction between the 7-amino-8-thiocephalosporanic acid of formula III and the acid is effected, for example, by dissolving or suspending the latter in an inert organic solvent such as chloroform, methylene chloride, dioxane, benzene or the like, and adding, at about room temperature or below, about an equimolar amount of an anhydride forming reagent, e.g., ethyl chloroformate, benzoylchloride or the like, or other activating compound such as dicyclohexylcarbodiimide, along with a salt forming organic base, such as triethylamine, pyridine or the like, followed, after an interval, by the addition of the 7-amino-8-thioxocephalosporanic acid or derivative. The product of the reaction is then isolated by conventional procedures, e.g., by concentration or evaporation of the solvent.

Further process detail are also provided in the illustrative examples.

Certain of the compounds of this invention may exist in different optically active forms. The various stereoisomeric forms as well as the racemic mixtures are within the scope of the invention.

The compounds of this invention are useful as antimicrobial agents because of their activity against organisms such as *Streptococcus pyrogenes* and *Candida albicans*. They can be used to combat infections due to organisms such as those named above, and in general may be utilized in a manner smilar to cephradine and other cephalosporins. For example, a compound of formula I or a physiologically acceptable salt thereof can be used in various animal species in an amount of about 1 to 200 mg/kg, daily, orally or parenterally, in single or two to four divided doses to treat infections of bacterial origin, e.g., 5.0 mg/kg is effective in mice. Up to about 600 mp. of a compound of formula I or a physiologically acceptable salt thereof is incorporated in an oral dosage form such as tablet, capsule or elixir or in an injectable form in a sterile aqueous vehicle prepared according to conventional pharmaceutical practice.

The following examples are illustrative of the invention and are preferred embodiments. They also serve as models for additional variations which are produced in the same manner by appropriate substitution of the starting material. All temperatures are in degrees celsius.

EXAMPLE 1

3-Methyl-7β-[(phenoxyacetyl)amino]-8-thioxo-5-thia-1-azabicyclo[4.2.0]oct-2-ene-2-carboxylic acid, 2,2,2-trichloroethyl ester 2,2,2-Trichloroethyl-7-phenoxyacetamido-3-methyl-3-cephem-4-carboxylate is prepared according to the method of R.R. Chauvette, et al., J. Org. Chem. 36, 1259 (1971). This ester (7.60 g., 16 mmoles) is dissolved in 50 ml. of dry chloroform and boron sulfide (3.80 gm., 32 mmoles) is added. The mixture is gently refluxed under nitrogen overnight. The reaction mixture is filtered and the solvent is removed under reduced pressure. The resultant residue is chromatographed on silica gel (40:1) using chloroform-benzene. A fraction containing 400 mg. of 2,2,2-trichloroethyl-7-phenoxyacetamido-8-thioxo-3-methyl-3-cephem-4-carboxylate free of contaminants is obtained. Analytically pure material is obtained by silica gel thin layer chromatography using 2% ethyl acetate in chloroform. The product 3-methyl-7β-[(phenoxyacetyl)amino]-8-thioxo-5-thia-1-azabicyclo[4.2.0]oct.-2-ene-carboxylic acid, 2,2,2-trichloroethyl ester is isolated as a yellow foam.

EXAMPLE 2

3-Methyl-7β-[(phenylacetyl)amino]-8-thioxo-5-thia-1-azabicyclo[4.2.0]oct-2-ene-2carboxylic acid, trichloroethyl ester 2,2,2-Trichloroethyl-7-phenylacetamido-3-methyl-3-cephem-4-carboxylate (3 g., 6.47 mmole) is dissolved in 20 ml. of dry chloroform and boron sulfide (1.53 g., 12.94 mmole) is added. The mixture is refluxed under nitrogen until thin layer chromatography (2% ethyl acetate in chloroform on silica gell shows no further reaction. The mixture is filtered to remove solids and the solvent is removed under reduced pressure. The residue is placed on a silica gel column and eluted with benzene-chloroform to remove further impurities. A concentrate of this eluate is placed on silica gel preparative thin layer chromatography plates and developed with 2% ethyl acetate in chloroform in order to remove starting material. Final purification is effected by crystallization from ether to give 3-methyl-7β-[(phenylacetyl)amino]-8-thioxo-5-thia-1-azabicyclo[4.2.0]-oct-2-ene-2-carboxylic acid, trichloroethyl ester as pale yellow needles, m.p., 150°–151°; yield 123 mg. (4%).

EXAMPLE 3

3-Methyl-7β-[(phenoxyacetyl)amino]-8-thioxo-5-thia-1-azabicyclo[4.2.0]oct-2-ene-2-carboxylic acid The product of Example 1 (400 mg.) is dissolved in 90% aqueous acetic acid and zinc dust (670 mg., 25 eq.) is added. The mixture is stirred at room temperature for 2.5 hours. The mixture is filtered into a mixture of 150 ml. of ethyl acetate and 75 ml. of water. The organic layer is washed five times with 50 ml. portions of water. 75 ml. of water is added and aqueous sodium hydroxide is added until the pH is adjusted to 8. The aqueous layer is then washed with 25 ml. of ethyl acetate. 150 ml. of ethyl acetate is added to the aqueous layer and the pH is adjusted to 2.5. The organic layer is washed with water, dried over magnesium sulfate, filtered, and the solvent is removed under reduced pressure. The product 3-methyl-7β-[(phenoxyacetyl- )amino]-8-thioxo-5-thia-1-azabicyclo[4.2.0oct-2-ene-2-carboxylic acid is obtained as a yellow foam and used without further purification.

EXAMPLE 4

3-Methyl-7β-[(phenylacetyl)amino]-8-thioxo-5-thia-1-azabicyclo-[4.2.0]oct-2-ene-2-carboxylic acid The ester from Example 2 (650 mg., 1.35 mmole) is placed in 40 ml. of aqueous acetic acid and zinc dust (1 g., 1.54 mmole) is added. The mixture is stirred at room temperature until analysis by thin layer chromatography (silica gel using 2% ethyl acetate in chloroform) shows only small amounts of starting material remaining. The reaction mixture is poured into a mixture of 100 ml. of ethyl acetate and 20 ml. of water. The organic layer is washed five times with 20 ml. portions of water to remove acetic acid. The organic layer is treated with 100 ml. of water and aqueous sodium hydroxide is added until the pH is adjusted to 8. The aqueous layer is then washed with 25 ml. of ethyl acetate. 100 ml. of ethyl acetate are added and the pH is adjusted to 2.5 with hydrochloric acid. The organic layer is washed with water, dried over magnesium sulfate, filtered, and the solvent is removed under reduced pressure giving 200 mg. of product as a yellow foam. This product, 3-methyl-7β-[(phenylacetyl)amino]-8-thioxo-5-thia-1-azabicyclo[4.2.0]-oct-2-ene-2-carboxylic acid, is recrystallized from ethyl acetate-petroleum ether to give yellow crystals, m.p. 176°–176.5°; yield 80 mg. (17%).

EXAMPLE 5

8-Thioxo-7-phenoxyacetamidocephalosporanic acid, 2,2,2-trichloroethyl ester 10 g. (1.86 mmoles) of 2,2,2-trichloroethyl 7-phenoxyacetamidocephalosporanate ($\Delta^2$ and $\Delta^3$ mixture of isomers) are refluxed with boron sulfide (4.40 g., 3.72 mmoles) in dry chloroform (100 ml.) under nitrogen overnight. The reaction mixture is allowed to cool and filtered to remove solids. Solvent is removed from the filtrate under reduced pressure and the residue is eluted through 200 g. of silica gel with methylene chloride changing to chloroform.

The fractions which come out just prior to starting material are collected and placed on preparative silica gel thin layer chromatography plates and eluted with chloroform. The band just above the starting material is collected with ethyl acetate. This thin layer chromatography purification procedure is repeated a total of three times until 70 mg. (0.7%) of product, 8-thioxo-7-phenoxyacetamidocephalosporanic acid, 2,2,2-trichloroethyl ester is obtained.

EXAMPLE 6

7-Thioxo-7-phenoxyacetamidocephalosporanic acid 2,2,2-Trichloroethyl-8-thioxo-7-phenoxyacetamidocephalosporanate (52 mg.) is dissolved in 5 ml. of 90% aqueous acetic acid. Zinc dust (78 mg., 12 eq.) is added and the reaction mixture is stirred at 0° for 45 minutes. The reaction mixture is added to a mixture of 10 ml. of cold water and 25 ml. of cold ethyl acetate. The aqueous layer is discarded and the organic layer is washed with 5 ml. of cold water. 15 ml. of cold water is added and the pH is adjusted to 7.5 with aqueous potassium hydroxide. The aqueous layer is treated with 25 ml. of cold ethyl acetate and the pH is adjusted to 2 with concentrated hydrochloric acid. The organic layer is dried over magnesium sulfate, filtered, and solvent removed in vacuo giving 23 mg. (44%) of 8-thioxo-7-phenoxyacetamidocephalosporanic acid as a yellow foam.

EXAMPLE 7

3-Methyl-7β-amino-8-thioxo-5-thia-1-azabicyclo [4.2.0]oct-2-ene-2-carboxylic acid 2,2,2-trichloroethyl ester The product of Example 2 (50 mg., 0.144 mmole) is dissolved in dry benzene (10 ml.), then dry pyridine (16 mg., 0.212 mmoles) and phosphorus pentachloride (44 mg., 0.212 mmoles) are added. The resultant solution is heated to 65° under nitrogen for two hours. The benzene is then removed in vacuo and replaced with methanol (6 ml.). This mixture is stored at room temperature under nitrogen overnight. The methanol is removed under reduced pressure and replaced by a mixture of water-tetrahydrofuran. This is stirred at room temperature for 15 minutes and the aqueous solution is treated with ethyl acetate and the pH is adjusted to 7 with sodium hydroxide. The ethyl acetate layer is separated, washed with water and dried over magnesium sulfate. The solvent is removed under vacuum to obtain 3-methyl-7β-amino-7-thioxo-5-thia-1-azabicyclo[4.2.0]oct-2-ene-2-carboxylic acid 2,2,2-trichloroethyl ester.

EXAMPLE 8

3-Methyl-7-amino-8-thioxo-5-thia-1-azabicyclo[4.2.-0]oct-2-ene-2-carboxylic acid The product of Example 7 is treated as described in Example 6. The final, basic, aqueous solution is adjusted to pH 3.65 with 2N hydrochloric acid and extracted with ethyl acetate. Drying and removal of the solvent under vacuum gives 3-methyl-7-amino-8-thioxo-5-thia-1-azabicyclo-[4.2.0]oct-2-ene-2-carboxylic acid.

EXAMPLE 9

3-Methyl-7β-[(phenoxyacetyl)amino]-8-thioxo-5-thia-1-azabicyclo[4.2.0]oct-2-ene-2-carboxylic acid, 2,2,2-trichloroethyl ester A solution of the product of Example 7 in ethyl acetate is stirred with an excess of solid sodium bicarbonate and a slight excess of phenoxyacetyl chloride is added. After several hours at room temperature, the solution is filtered, concentrated, and applied to a silica gel TLC plate. Development with chloroform-2% ethyl acetate, elution of the UV-active major band, and removal of the solvent under vacuum gives 15 mg. of material, identical by IR, NMR and UV with the product of Example 1.

EXAMPLE 10

3-Methyl-7β-[(2-thienylacetyl)amino]-8-thioxo-5-thia-1-azabicyclo[4.2.0]oct-2-ene-2-carboxylic acid A solution of 1.1 mmole of the product of Example 8 in 10 ml. of 50% aqueous acetone at 0° containing 3.3 ml. of 1N sodium bicarbonate is treated with 1.1 mmole of (2-thienyl)acetyl chloride. After four hours, the solution is diluted with chloroform, acidified to pH 2.5, and the chloroform layer is dried and evaporated to give 3-methyl-7β-[(2-thienylacetyl)amino]-8-thioxo-5-thia-1-azabicylco[4.2.0]oct-2-ene-2-carboxylic acid.

The following additional products are made by the procedure of Example 1, substituting the β-lactam precursor of the product as starting material, and where R is hydrogen, the trichloroethyl ester is cleaved as described in Example 3.

TABLE

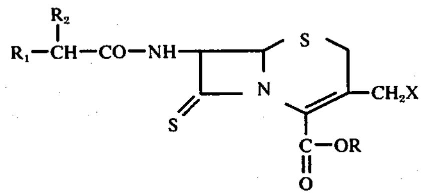

| Example | R | $R_1$ | $R_2$ | X |
|---|---|---|---|---|
| 10 | $CH_3$— | H | H | H |
| 11 | $C_2H_5$— | $CH_3$— | H | —$OCOCH_3$ |
| 12 | $CCl_3CH_2$— | $C_3H_7$— | H | —S—$CH_3$ |
| 13 | $CHCl_2CH_2$— | $C_6H_5CH_2$— | H | —$OCOCH_3$ |
| 14 | $CCl_3CH_2$— | $C_6H_5CH_2$— | H | 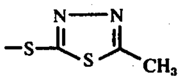 |
| 15 | $CCl_3CH_2$— | $C_6H_5$— | H | —$OCOCH_3$ |
| 16 | H | $C_6H_5$— | $NH_2CONH$— | —S—$CH_3$ |
| 17 | $CCl_3CH_2$— | $C_6H_5$— | H | 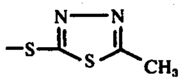 |
| 18 | $CCl_3CH_2$— | $C_6H_5$ | H | 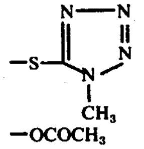 |
| 19 | H | 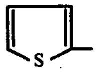 | $NH_2CONH$— | —$OCOCH_3$ |
| 20 | H | 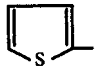 | COOH | H |
| 21 | H | 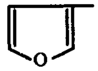 | H | H |
| 22 | —$CH_2CCl_3$ | 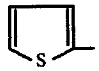 | H | H |
| 23 | $C_6H_5CH_2$— | 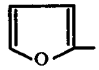 | H | H |
| 24 | H | 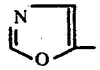 | H | —S—$CH_3$ |
| 25 | K | $C_6H_5$—O— | H | 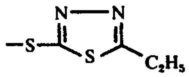 |
| 26 | Na | $C_6H_5$—O— | H | 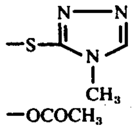 |
| 27 | H | 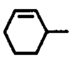 | H | —$OCOCH_3$ |

The following products are made by substituting the acylating agent in the last column for the phenoxyacetyl chloride and sodium bicarbonate on the procedure of Example 9, followed by removal of the trichloroethyl ester as described in Example 3:

| Example | R | $R_1$ | $R_2$ | X | Acylating Agent |
|---|---|---|---|---|---|
| 27 | H | 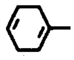 | H | H | 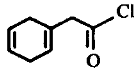 |
| 28 | H | 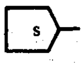 | H | H | 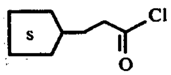 |

-continued

| Example | R | $R_1$ | $R_2$ | X | Acylating Agent |
|---|---|---|---|---|---|
| 29 | H | 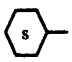 | H | H | 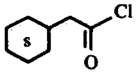 |

EXAMPLES 30 – 32

Following the procedure of Example 7, but substituting the compound in column I for the compound of Example 2, the compound in column II is obtained:

| Example | Column I | Column II |
|---|---|---|
| | | 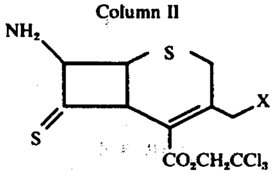 |
| | | X |
| 30 | Compound of Example 5 | $-OCOCH_3$ |
| 31 | Compound of Example 17 | 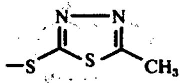 |
| 32 | Compound of Example 18 | 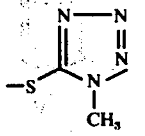 |

EXAMPLES 33 – 35

Following the procedure of Example 8, and substituting the compound of column I for the compound of Example 7, the compound of column II is obtained:

| Example | Column I | Column II |
|---|---|---|
| | | 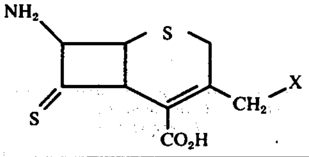 |
| | | X |
| 33 | Compound of Example 6 | $-OCOCH_3$ |
| 34 | Compound of Example 31 | 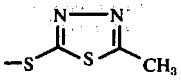 |
| 35 | Compound of Example 32 | 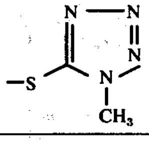 |

EXAMPLES 36 – 47

Following the procedure of Example 10, but substituting the compound of column I for the compound of Example 8 and the acid chloride in column II for phenoxyacetyl chloride, the compound of column III is obtained:

| Example | Column I | Column II | Column III | |
|---|---|---|---|---|
| | | | 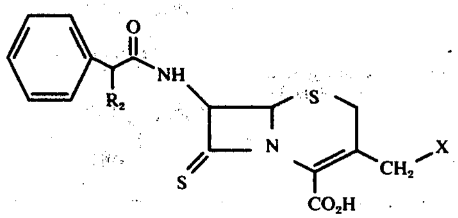 | |
| | | | $R_2$ | X |
| 36 | Compound of Example 8 | 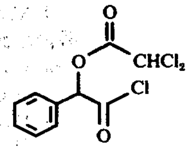 | OH | H |
| 37 | Compound of Example 33 | 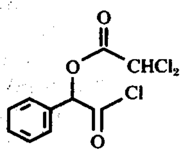 | OH | $-OCOCH_3$ |
| 38 | Compound of Example 34 | 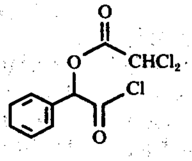 | OH | 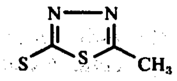 |

-continued

| Example | Column I | Column II | Column III | |
|---|---|---|---|---|
| | | | 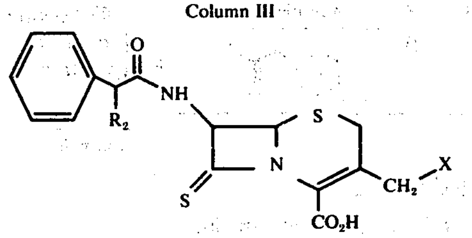 | |
| 39 | Compound of Example 35 | 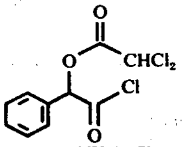 | OH | 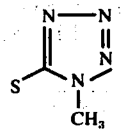 |
| 40 | Compound of Example 8 | 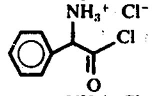 | $NH_2$ | H |
| 41 | Compound of Example 33 | 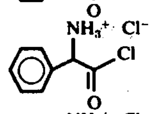 | $NH_2$ | $-OCOCH_3$ |
| 42 | Compound of Example 34 | 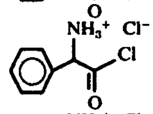 | $NH_2$ | 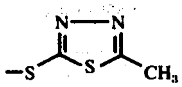 |
| 43 | Compound of Example 35 | 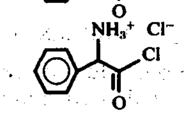 | $NH_2$ | 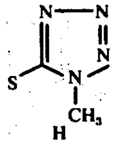 |
| 44 | Compound of Example 8 | 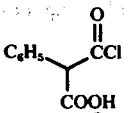 | COOH | H |
| 45 | Compound of Example 33 | 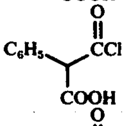 | —COOH | $-OCOCH_3$ |
| 46 | Compound of Example 34 | 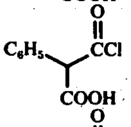 | —COOH | 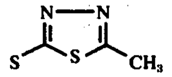 |
| 47 | Compound of Example 35 | 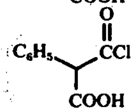 | —COOH | 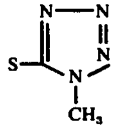 |

What is claimed:

1. A compound of the formula

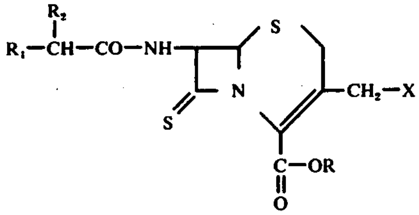

wherein R is hydrogen, lower alkyl, phenyl-lower alkyl, trihaloethyl, alkali metal or alkaline earth metal; $R_1$ is hydrogen, lower alkyl, saturated or unsaturated cycloalkyl of 3 to 7 carbons, phenyl, phenyl-lower alkyl, phenoxy, thienyl, furyl, oxazolyl, isoxazolyl, or thiazolyl; $R_2$ is hydrogen, amino, carboxy, hydroxy or ureido; and X is lower alkyl thiadiazolyl thio or lower alkyltetrazolyl thio.

2. A compound as in claim wherein R is hydrogen, alkali metal or trichloroethyl; $R_1$ is hydrogen, phenyl, thienyl or furyl; $R_2$ is hydrogen, amino or hydroxy and X is 1-methyl-1H-tetrazol-5-ylthio.

3. A compound as in claim 1 wherein $R_1$ is phenyl.

4. A compound as in claim 1 wherein $R_1$ is thienyl.

5. A compound as in claim 2 wherein R and $R_2$ each is hydrogen.

6. A compound as in claim 3 wherein R and $R_2$ each is hydrogen and X is 1-methyl-1H-tetrazol-5-ylthio.

7. A compound as in claim 3 wherein R and $R_2$ each is hydrogen and X is 5-methyl-1,3,4-thiadiazol-2-yl thio.

8. A compound as in claim 3 wherein R is hydrogen, $R_2$ is amino and X is 1-methyl-1H-tetrazol-5-ylthio.

9. A compound as in claim 3 wherein R is hydrogen, $R_2$ is carboxy and X is 1-methyl-1H-tetrazol-5-ylthio.

* * * * *